United States Patent [19]
Lin

[11] Patent Number: 5,834,313
[45] Date of Patent: Nov. 10, 1998

[54] CONTAINER MONITORING SYSTEM

[75] Inventor: Szu-Min Lin, Laguna Hills, Calif.

[73] Assignee: Johnson & Johnson Medical, Inc., New Brunswick, N.J.

[21] Appl. No.: 934,496

[22] Filed: Sep. 19, 1997

[51] Int. Cl.$^6$ .................................................. G01N 31/22
[52] U.S. Cl. .................................. 436/1; 422/28; 422/26; 422/61; 436/127
[58] Field of Search .................... 422/28, 26, 34–37, 422/61; 436/1, 127–131

[56] References Cited

U.S. PATENT DOCUMENTS 4,580,682  4/1986  Gorski et al. ............................ 206/569
5,160,700  11/1992  Anderson et al. ........................ 422/34

Primary Examiner—Lyle A. Alexander
Attorney, Agent, or Firm—Knobbe, Martens, Olson & Bear, LLP

[57] ABSTRACT

A sterilization system using a sterilization process monitoring device which is capable of indicating the efficacy of the sterilization process in an enclosed sterilization container while still maintaining the sealed state of the sterilization container. The process monitoring device comprises at least one biological indicator and/or at least one chemical indicator. Upon completion of the sterilization cycle, the process monitoring device can be advantageously removed from the system to determine chemical and/or biological efficacy of the sterilization process. The removal of the biological and/or chemical indicators does not disturb the sterilized state of the articles inside the sterilization container.

32 Claims, 12 Drawing Sheets

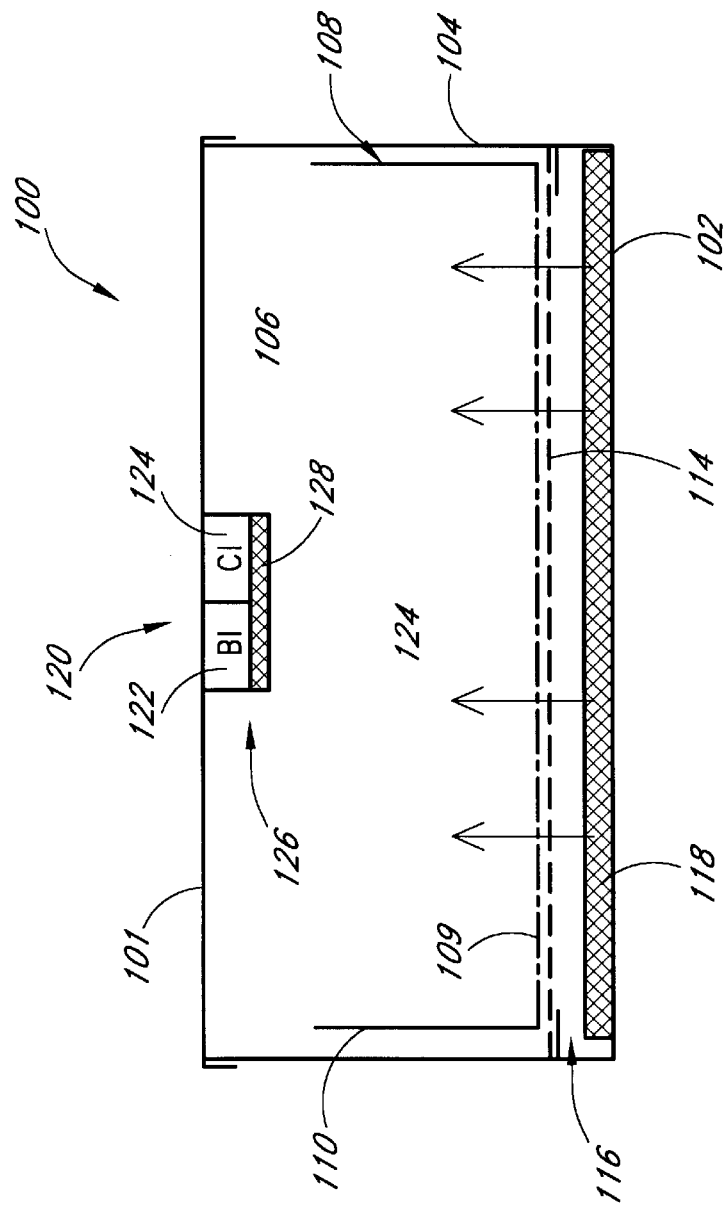
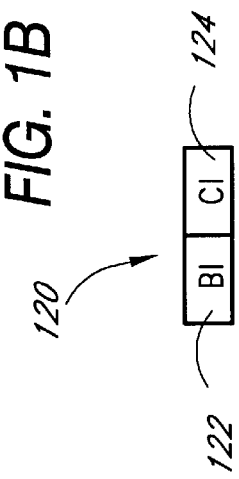
FIG. 1A
FIG. 1B

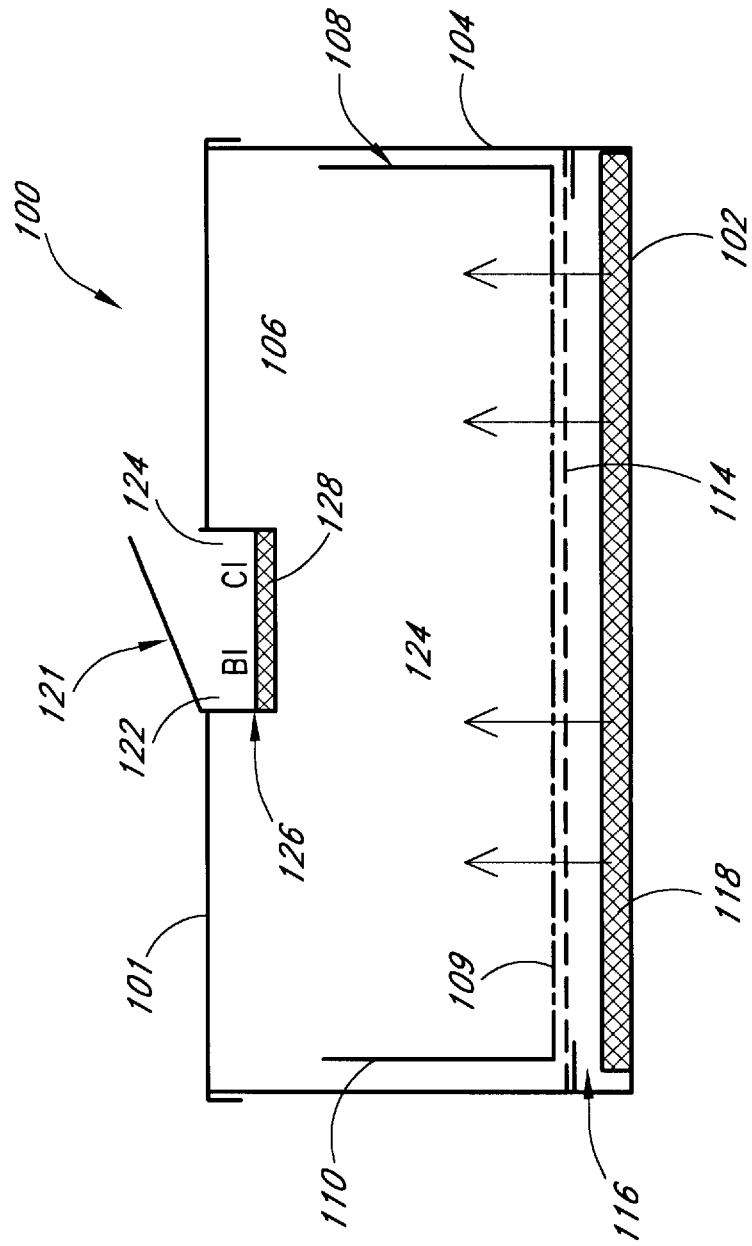

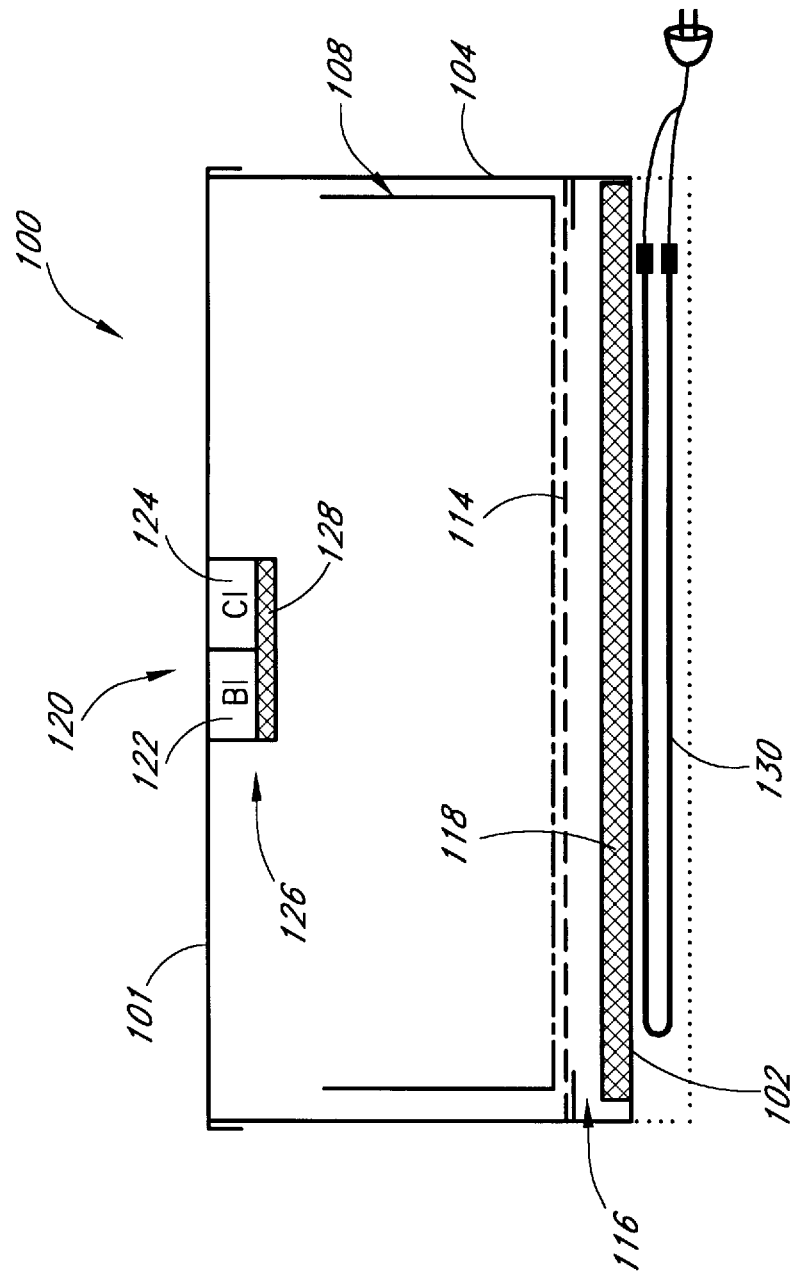

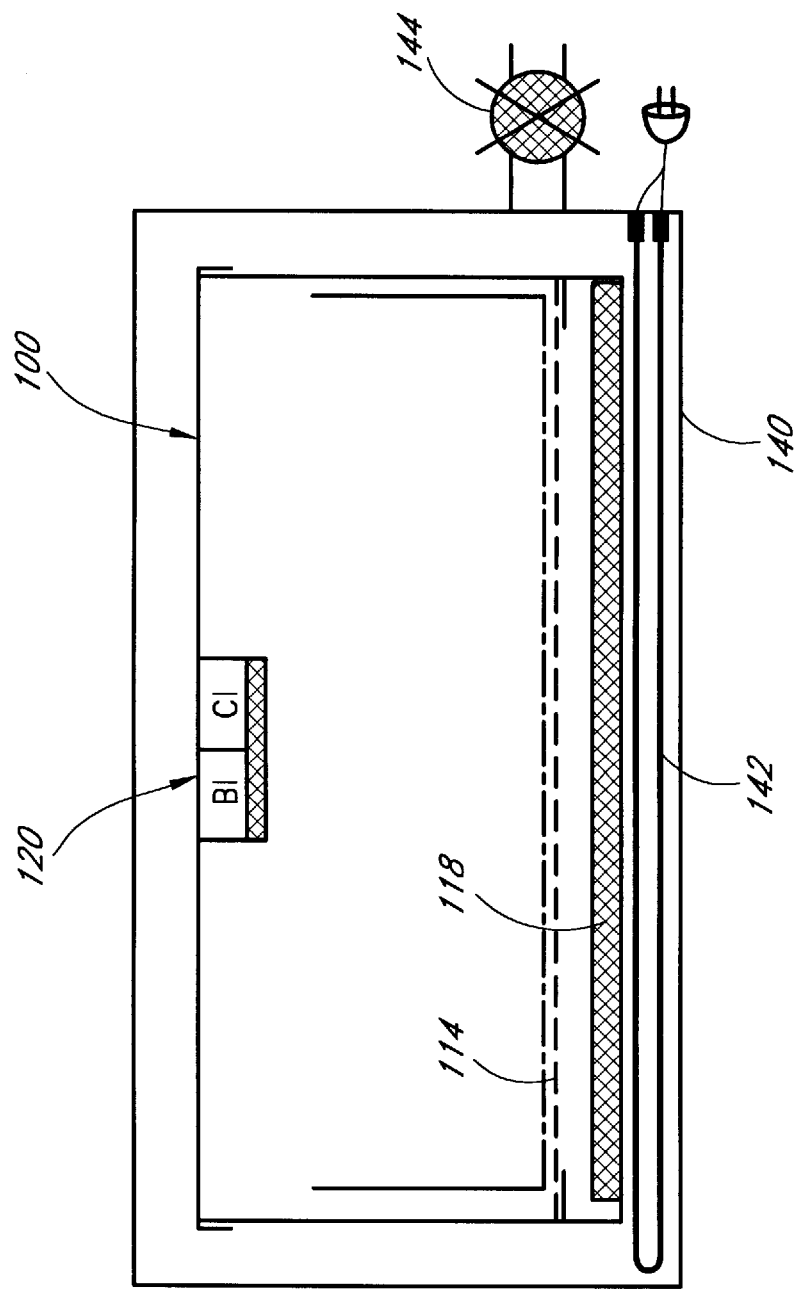

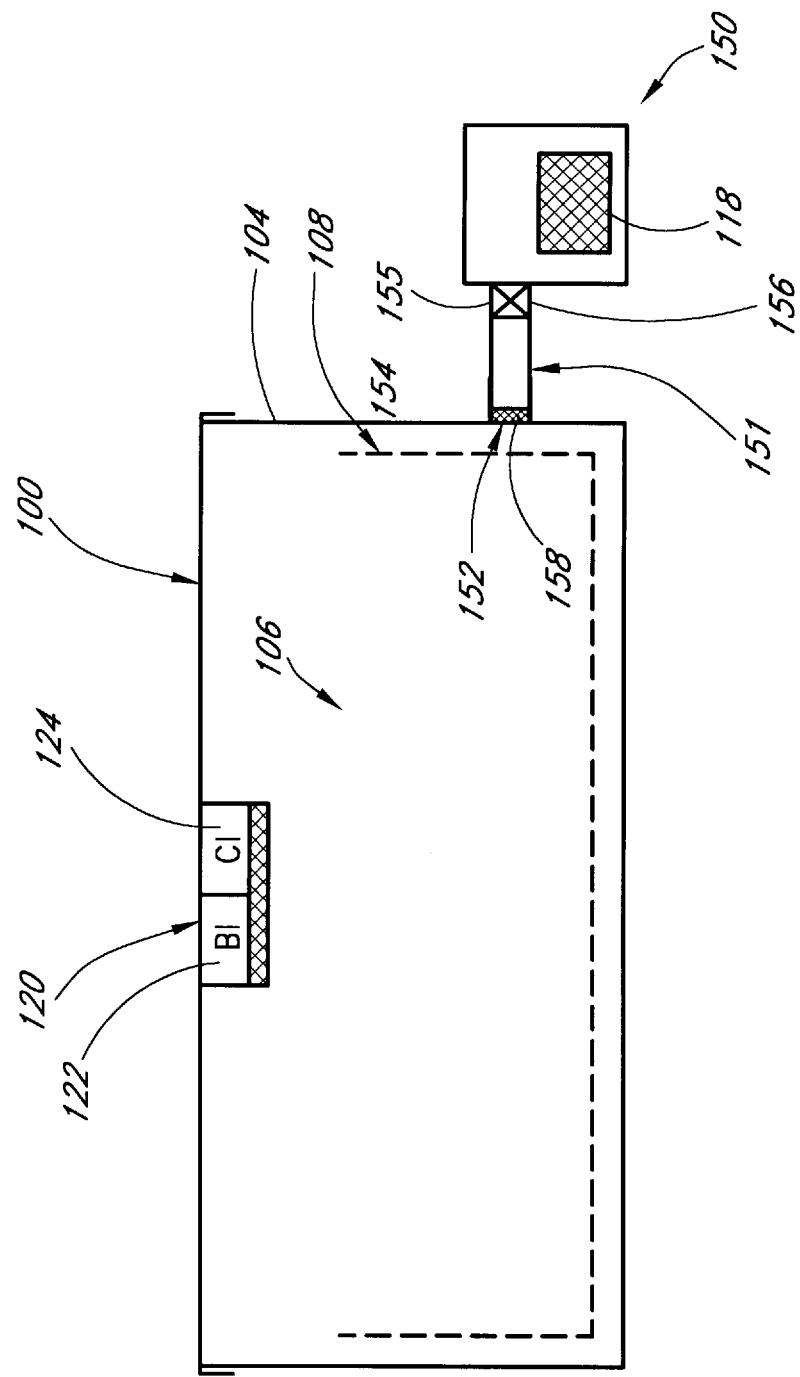

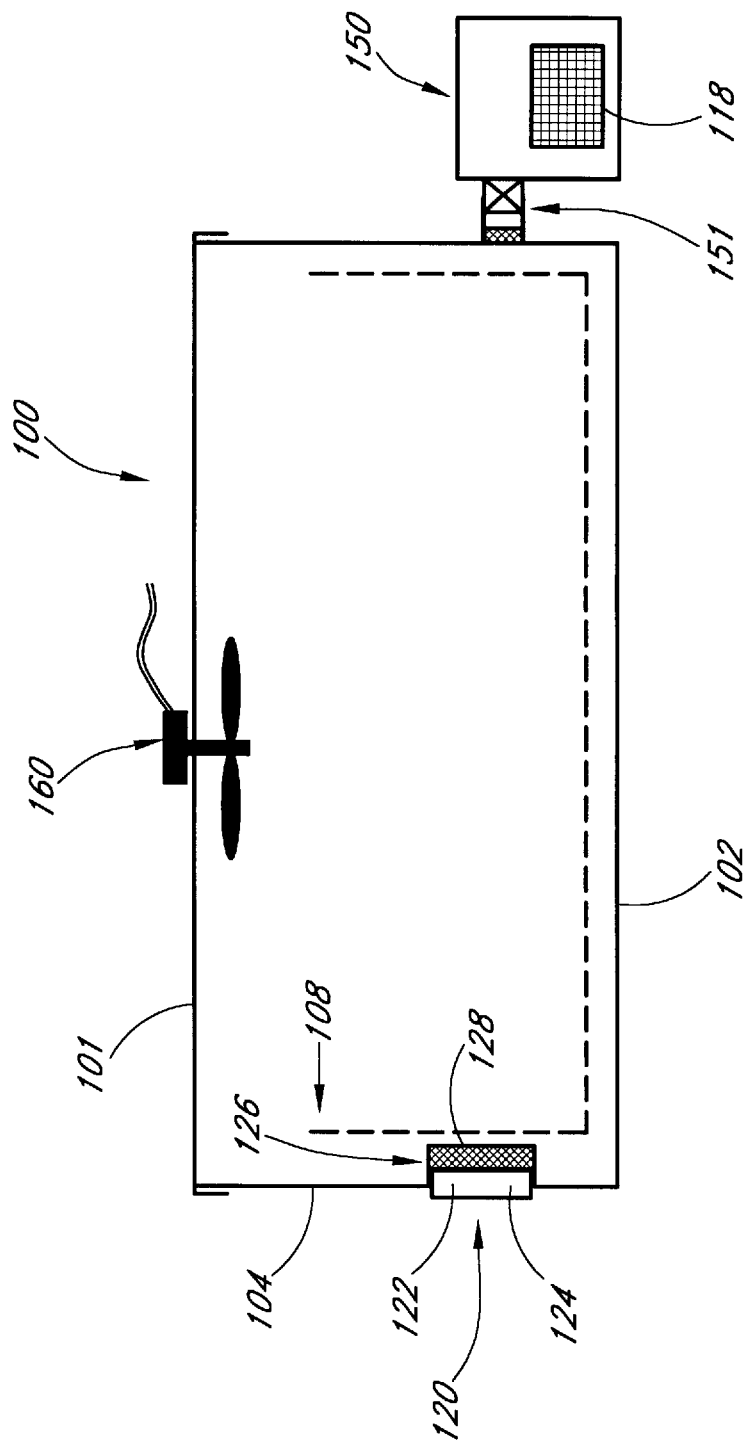

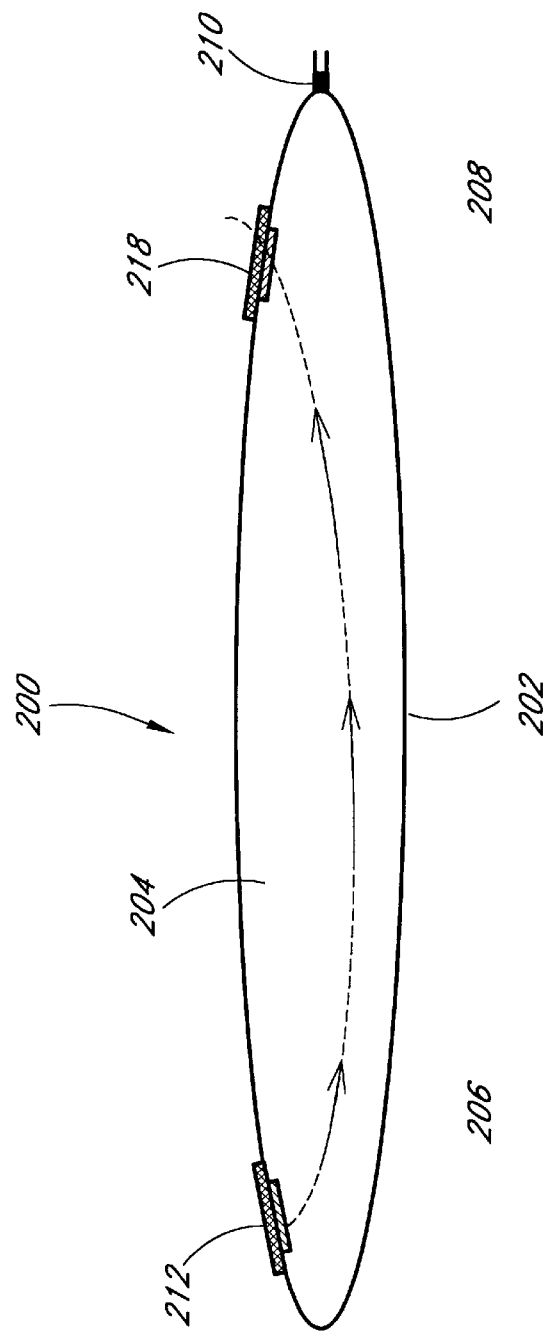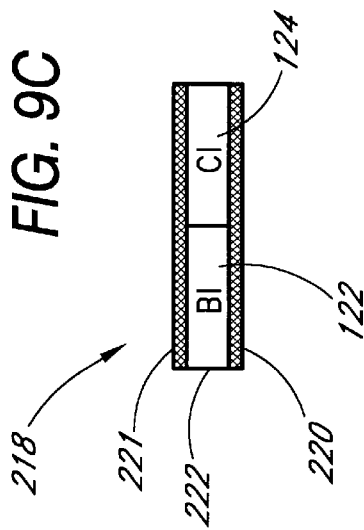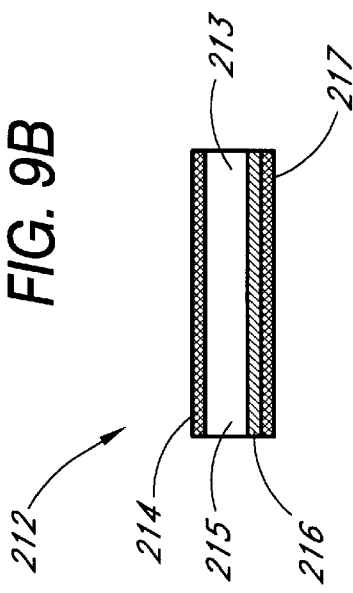

CONTAINER MONITORING SYSTEM

BACKGROUND OF THE INVENTION

1. Field of the Invention

The present invention generally relates to sterilization processes, and more particularly, to the techniques for monitoring the efficacy of a container system.

2. Description of the Related Art

A sterilization process generally involves in exposing the articles to be sterilized to a sterilizing medium that can kill bacterial microorganisms. Such processes are performed in sterilization chambers. The articles to be sterilized are often delivered to the sterilization chambers within a sterilization container in which the articles are both sterilized and subsequently stored in their sterilized state.

The sterilization containers are generally permeable to a sterilizing medium so that the sterilizing medium may enter the container during the sterilization process. A sterilizing medium may be a sterilant gas or vapor (e.g., hydrogen peroxide vapor) released by a sterilant source which is placed into or delivered into the sterilization container. As used hereinafter, the terms "gas" and "vapor" are used interchangably. Such gas permeable containers may, for example, include pouches made of gas permeable materials or rigid trays wrapped with gas permeable wraps. In fact, a sterilization container may be configured as a sealable rigid container having ports to deliver a sterilant after the container has been sealed. In all above examples, however, the sterilization containers prevent the entry of the microorganisms into the container and thereby maintain the sterilized state of the articles therein.

In modern medical and dental practice, it is important to monitor the efficacy of the sterilization processes. That is, at the end of the sterilization cycle, it must be verified that all of the articles have been adequately exposed to the sterilizing medium and the existing microorganisms have been killed. Conventional sterilization processes commonly have two underlying monitoring devices that address such concerns, namely, biological indicators and chemical indicators. A biological indicator (BI) is a type of device having a source of microorganisms. In this context, the source of microorganisms refers to a predetermined concentration of microorganisms which are generally impregnated into a paper strip. A biological indicator is used to monitor the sterilization process and determine whether the particular sterilant succeeded in killing all the microorganisms in the load to be sterilized. In practice, the biological indicator is maintained in a gas permeable pack which is made of gas permeable materials. During the sterilization process, the biological indicators are conventionally placed outside the sterilization containers so that the biological indicator can be retrieved without compromising the sterility of the devices within the container. After exposure to the sterilization process, the source of microorganisms is placed in a sterile culture medium and incubated for a pre-determined period of time. Any surviving microorganisms indicates the incompleteness of the sterilization process in the container.

On the other hand, chemical indicators (CI) are devices that primarily indicates whether or not the sterilization process cycle is carried out properly to deliver the sterilant to the sterilization chamber. Thus, chemical indicators do not provide a true indication that sterility has been achieved. Chemical indicators contain specific chemical compositions which chemically reacts and change color when exposed to the sterilizing medium. Additionally, chemical indicators may be designed to include and respond to a plurality of sterilization process parameters. For example, a chemical indicator can be designed to indicate or respond to certain sterilant concentrations, humidity, time, temperature, sterilant's pH or pressure.

During conventional sterilization processes, biological and chemical indicators are typically placed outside the gas permeable sterilization containers in which the load of the articles to be sterilized are placed. Upon completion of the sterilization process, containers, which are in their sealed state and with a presumably sterilized load, are often stored for a period of time before the sterilized articles are needed. In such conventional processes, the actual state of the sterilization inside the container is determined by inspecting the indicators located outside the container to determine whether the sterilization has been achieved. However, in practice, this approach has serious drawbacks because these indicators cannot provide accurate information about the sterilization status of the articles in the container. Since the indicators only display the outside readings, there is no way of knowing whether sterilization has occurred inside the container.

An alternative approach utilizes two chemical indicators to overcome the above given drawback. In this approach one of the chemical indicators is placed into the container adjacent to the load of articles. Unfortunately, the problem with this approach is that the actual state of the sterilization can only be determined by opening the container and inspecting the chemical indicator placed inside the container. However, this is also not practical and disturbs the sealed state of the container and the sterility of the devices therein. There also is a possibility that sterilization conditions were not achieved inside the container. Accordingly, throughout the storage period, the actual state of the sterilization process cannot be known.

Some container systems have a clear barrier through which a chemical indicator, but not a biological indicator, can be read. However, such chemical indicators cannot be removed without breaking the barrier. Moreover, in such a system, the chemical indicator is included within the load, so it is exposed to sterilant at the same time as the load. As a result, the chemical indicator may indicate a sterile result, even when portions of the load have not been exposed to sufficient sterilant to achieve sterility.

In view of the foregoing, there is a need for a new monitoring system for sterilization processes which is capable of indicating the state of the sterilization in an enclosed sterilization container while maintaining the sealed state of the sterilization container.

SUMMARY OF THE INVENTION

The aforementioned needs are satisfied by the system of the present invention which comprises a sterilization system using a sterilization process monitoring device which is capable of indicating the efficacy of the sterilization process in an enclosed sterilization container while still maintaining the sealed state of the sterilization container.

In one aspect of the present invention, a system for monitoring a sterilization process is provided. The system is comprised of a container, a sterilant source and at least one indicator. The container is adapted to receive articles to be sterilized wherein the container includes at least one gas permeable material on an outer wall of the container so as to allow a sterilant gas to diffuse through the gas permeable material. The sterilant source is adapted to provide the sterilant gas inside of the container. At least one indicator is positioned on at least one gas permeable material of the container so that the indicator receives the sterilant gas that diffuses through the gas permeable material wherein the gas permeable material prevents the penetration of microorganisms therethrough so that at least one indicator can be removed from the container without disturbing the sterilization process.

In another aspect of the present invention a method of monitoring a sterilization process is provided. The method is comprised of providing a container adapted to receive articles to be sterilized, providing a sterilant source adapted to provide said sterilant gas inside of said container and positioning at least one indicator on said at least one gas permeable material of said container so that said indicator receives said sterilant gas that diffuses through said gas permeable material. The container includes at least one gas permeable material on an outer wall of the container so as to allow a sterilant gas to diffuse through the gas permeable material. Further, the gas permeable material prevents the penetration of microorganisms therethrough so that at least one indicator can be removed from the container without disturbing the sterilization process.

These and other objects and advantages of the present invention will become more fully apparent from the following description taken in conjunction with the accompanying drawings.

BRIEF DESCRIPTION OF THE DRAWINGS

FIG. 1A is a schematic view of a first embodiment of a sterilization system comprising a sterilization container with an attachable process monitoring device;

FIG. 1B is a schematic detail view of the attachable process monitoring device;

FIG. 1C is a schematic view of a modified form of the first embodiment of the sterilization system in which a process monitoring device is provided within an openable housing.

FIG. 2 is a schematic view of a second embodiment of the sterilization system wherein the sterilization container comprises a heating source;

FIG. 5 is a schematic view of a fifth embodiment of the sterilization system wherein the sterilization container is placed into a vacuum oven;

FIG. 6A is a schematic view of a sixth embodiment of the sterilization system wherein the sterilization container comprises a separate sterilant enclosure;

FIG. 8 is a schematic view of an eighth embodiment of the sterilization system wherein the separate sterilant enclosure and the process monitor device are placed over the opposite sides of the sterilization container;

FIG. 9A is a schematic view of an alternative embodiment of the sterilization system comprising a flexible container with an attachable process monitor device and an attachable sterilant source cartridge;

FIG. 9B is a schematic view of the attachable sterilant source cartridge; and

FIG. 9C is a schematic view of the attachable process monitor device.

DETAILED DESCRIPTION OF THE PREFERRED EMBODIMENT

Figure 3:
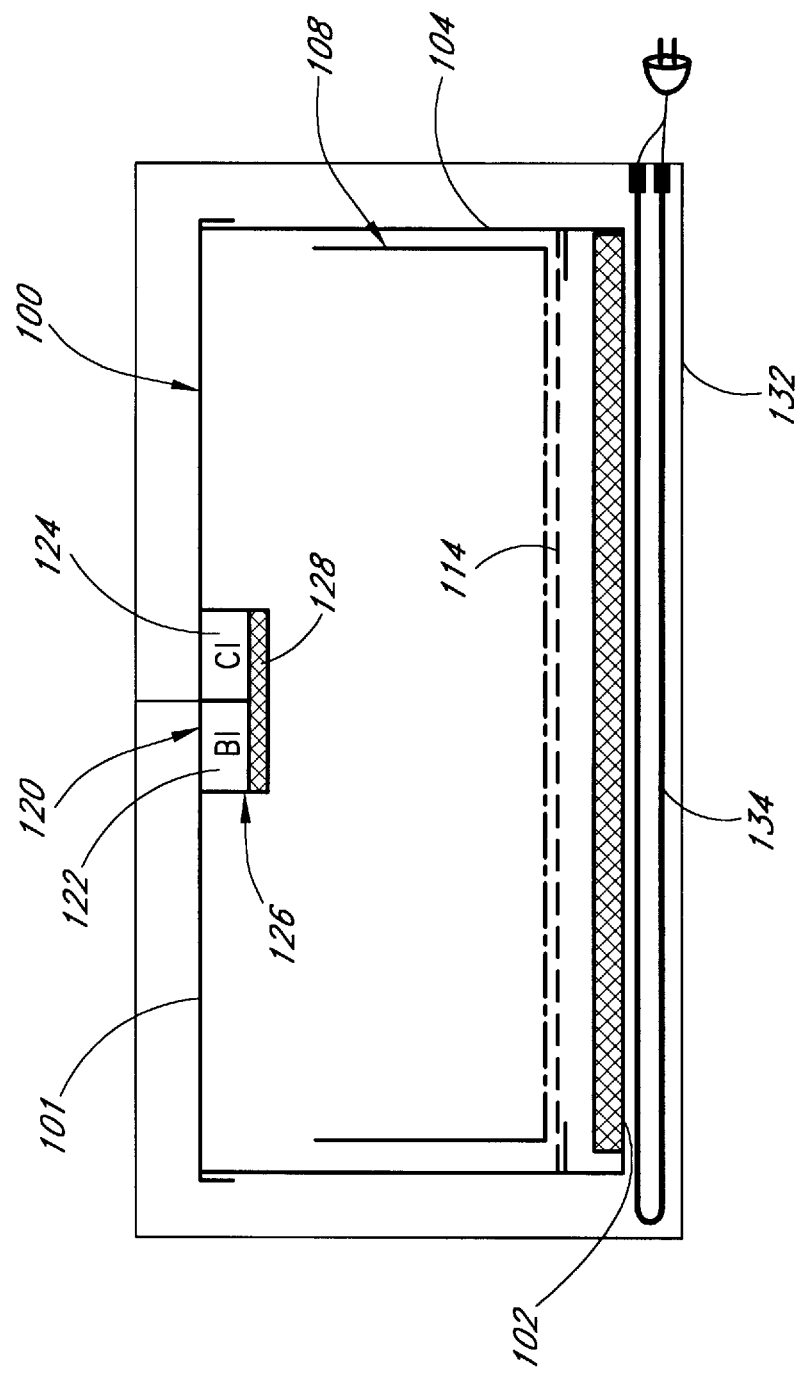
FIG. 3 is a schematic view of a third embodiment of the sterilization system wherein the sterilization container is placed into an oven.

As an improvement to conventional monitoring systems for sterilization processes, the process of the preferred embodiments are preferably capable of indicating the efficacy of the sterilization process in an enclosed sterilization container while still maintaining the sealed state of the sterilization container. Reference will now be made to the drawings wherein like numerals refer to like parts throughout.

As illustrated in FIG. 1, sterilization system of the preferred embodiment comprises a first container 100. In the preferred embodiment, the first container 100 is preferably a rigid enclosed container comprising a top portion 101, a bottom portion 102 and a peripheral wall 104 which is preferably perpendicularly attached to the periphery of the bottom portion 102.

Preferred materials for manufacturing the solid container 100 may be metals or polymers such as aluminum, stainless steel or plastics. The bottom portion 102 and the peripheral wall 104 define a container housing 106. The container housing 106 may be preferably configured and dimensioned to receive at least one optional second container 108. The second container 108 may be configured as a tray having a perforated bottom 109 and a peripheral wall 110. The perforated bottom 109 and the peripheral wall 110 of the tray 108 define a second housing 112 to accommodate articles (not shown) to be sterilized. Inside the container housing 106, the tray 108 may be removably placed on an optional rack 114 which may be made of a perforated plate. Preferably, the rack 114 is removably attached to the inside of peripheral wall 104 so as to stay elevated from the bottom portion 102 of the container and so as to define a sterilant housing 116. A sterilant source 118 may be further placed into the sterilant housing 116 to produce a sterilizing medium such as a vapor sterilant. An exemplary sterilant source may be liquid peroxide, solid hydrogen peroxide complex and peracetic acid. A variety of solid peroxide complexes are described in allowed U.S. patent application Ser. No. 08/549,425, filed Oct. 27, 1995, the complete disclosure of which is hereby incorporated by this reference thereto. The top portion 101 of the container 100 comprises a removable container lid which seals the container housing 106 when closed.

As illustrated in FIGS. 1A–1B, in the preferred embodiment, a cartridge 120 comprising at least one process monitor device may be removably positioned onto the lid 101 of the container 100. In accordance with the principles of the present invention, these process monitor devices may comprise at least one biological indicator 122 and/or at least one chemical indicator 124. Either or both of these indicators can be provided with a unique identifier, such as a serial number, which pairs the indicator with the container. Thus, the container can be provided with the same identifier in order to pair it with the indicator.

As previously noted in the background section, the biological indicator 122 is kept in a gas permeable pack which permit the passage of the sterilizing gas but not the passage of microorganisms. In the preferred embodiment, such packs may, for example, be made of spun-bond polyethylene (e.g. Tyvek ™) or non-woven polypropylene wrap (e.g. CSR-wrap) materials. The cartridge 120 containing the biological and the chemical indicators 122 and 124 may be placed into a cartridge holder 126. The bottom layer of the cartridge 120 can optionally comprise a gas permeable material. The cartridge holder 126 may be configured to have a recessed cavity having a bottom 128 portion and downwardly extending into the container housing 106. The cartridge holder 126 may be dimensioned to receive at least one cartridge 120. In the preferred embodiment, the bottom portion 128 of the cartridge holder 126 is made of above-mentioned gas permeable materials (e.g., Tyvek™ or CSR-wrap) so that the sterilant vapor from the housing 106 can pass through the gas permeable material and reach indicators 122 and 124. The cartridge 120 may be secured in cartridge holder 126 by employing a number of fastening mechanisms such as snap-on type connectors or the like. However, with possible modifications in the cartridge 120 and the cartridge holder 126, the cartridge 120 may be secured to the holder 126 by a twist or a screw type of connector as well.

In the process of the preferred embodiment, the vapor sterilant such as hydrogen peroxide vapor diffuses through the rack 114 and the perforated bottom 109 of the tray 108 (in the direction of the arrows) and thereby contacting the articles and filling the container housing 106. While the sterilization process progresses, the sterilant vapor also diffuses through the gas permeable membrane 128 and subsequently into the cartridge 120 having the biological and/or chemical indicators 122 and 124. The sterilant vapor entering the cartridge 120 exposes indicators to the same sterilizing environment encountered by the articles in the tray 108. At this point, it is highly desirable that, on the container 100, the gas permeable membrane 128 of the holder 126 be accommodated at a farthest possible location from the sterilant source 118. As a result of this, the articles in the container 100 are treated with the sterilant vapor before the sterilant vapor diffuses through the gas permeable membrane 128. Since the indicators 122 and 124 are the last place for sterilant vapor to reach, they provide an accurate method of monitoring the sterilization status of the articles inside the container 100.

The sensitivity of the biological indicator and chemical indicator can be adjusted by adding features well known to those having ordinary skill in the art. A variety of such features are known which slow down the diffusion of sterilant. One example would be the Sterrad® Biological Indicator (BI) Test Pack, available from Advanced Sterilization Products (Irvine, Calif.).

In the present embodiment, upon completion of the sterilization cycle the cartridge 120 may be removed from the cartridge holder 126 to determine chemical and biological efficacy of the sterilization process. As opposed to prior art, however, the biological and/or chemical indicators can be removed from the container 100 without disturbing the sterilized state of the articles inside the sterilization container 100. Since the gas permeable layer 128 only allows the passage of the sterilant vapor, removal of the cartridge 120 from the holder 126 will not break the seal of the container 100.

Referring now to FIG. 1C, there is shown a modified form of the embodiment shown in FIG. 1A. In this embodiment, the biological indicator 122 and/or chemical indicator 124 are placed into a housing 126 with an openable or removable door 121. This modified form of this first embodiment can otherwise be constructed and used in accordance with the description provided above.

In addition, it is particularly advantageous to use the biological and chemical indicators 122 and 124 in separate cartridges. In such case, the chemical indicator may be furnished with a translucent or clear window which can display a written message, such as "PROCESSED" or a symbol such as "—", when the sterilization cycle is completed. Therefore, when the biological indicator is removed for detection, the chemical indicator may remain on the container and display the message to avoid any confusion during the storage. Alternatively, if the sterilization process uses more than one sterilant source, the number of chemical indicators can be increased accordingly. For example, if two chemicals are used as sterilant sources, the cartridge holder can be configured to have two chemical cartridges indicators and one or more biological indicator cartridges.

As will be explained more fully in the following embodiments, the release of the sterilant gas can be enhanced using heat or vacuum. FIGS. 2–9C illustrates alternative embodiments of the present invention. FIG. 2 illustrates a second embodiment of the sterilization system comprising the sterilization container 100 and a heat source 130. In accordance with the principles of the present invention, the heat source 130 may be configured as a part of the container 100 or positioned adjacent to the container 100 without being a part of the container 100. In this embodiment, the heat source 130 may be a heat element comprising a resistant wire which is attached to the bottom portion 102 of the sterilization container 100. Heat from the heat element 130 enhances the vaporization of the sterilant source 118 in the sterilant housing 116 and thereby enhancing the sterilization of the articles in the container 100.

FIG. 3 illustrates a third embodiment of the sterilization system comprising the sterilization container 100 placed into a third container 132. The third container 132 may be an oven having a heat source 134. In accordance with the principles of the present invention, the heat source 134 of the oven 132 may comprise infrared (IR) heating, radio frequency (RF) heating, microwave heating or resistant heating by heating elements. In the preferred embodiment, heating is provided by the heating elements 134.

Figure 4:
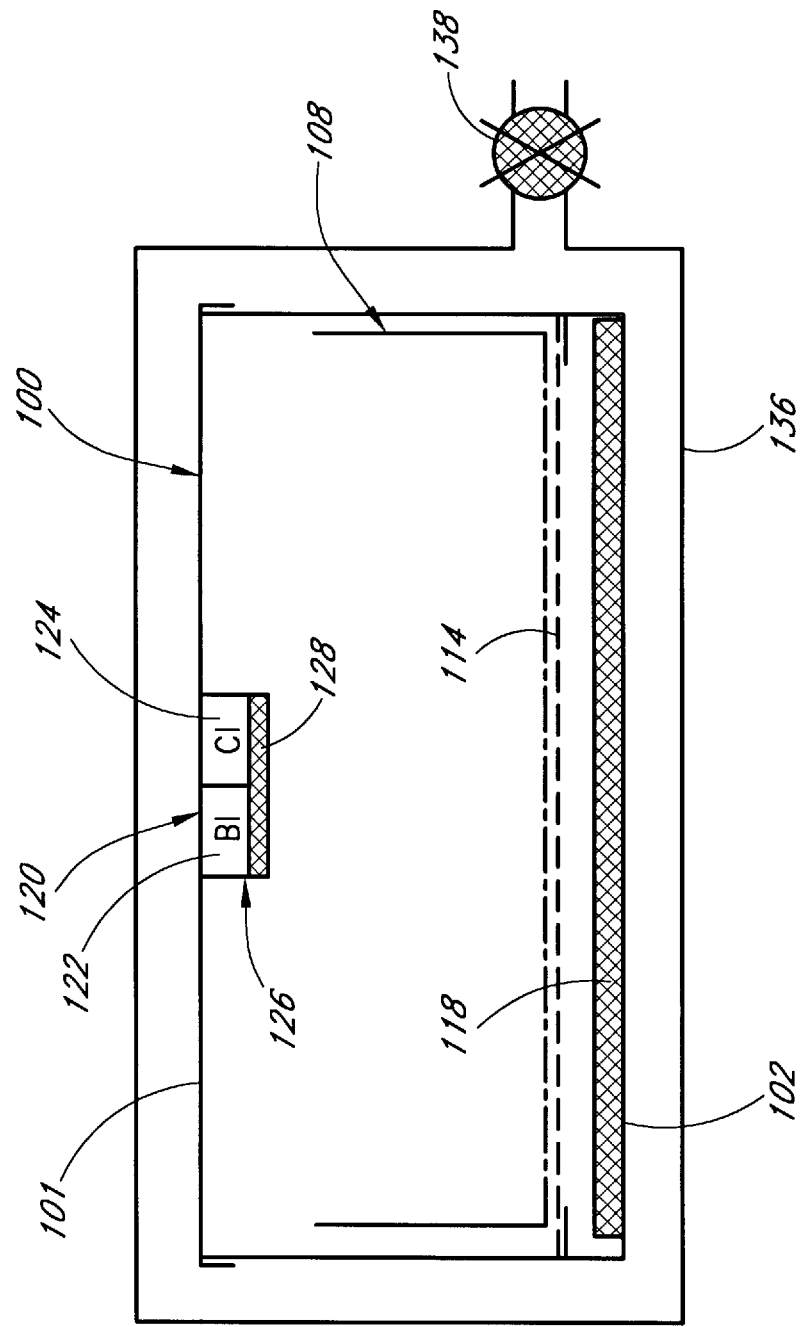
FIG. 4 is a schematic view of a fourth embodiment of the sterilization system wherein the sterilization container is placed into a vacuum chamber.

FIG. 4 illustrates a fourth embodiment of the sterilization system comprising the sterilization container 100 placed into a vacuum chamber 136 which is connected to a vacuum source (not shown) through a vacuum valve 138. The vacuum may also be used to enhance the vaporization of the sterilant source 118. Once the sterilization process is completed, the vacuum may also be used to remove the sterilant residues left on the articles.

FIG. 5 illustrates a fifth embodiment of the sterilization system comprising the sterilization container 100 placed into a vacuum oven 140. The vacuum oven is connected to a vacuum source (not shown) through a vacuum valve 144. The vacuum oven also comprises a heat source 142. In this embodiment, the combined effect of the vacuum and the heat enhances the vaporization of the sterilant source 118.

FIG. 6A illustrates a sixth embodiment of the sterilization system comprising the sterilization container 100. In this embodiment, the sterilization container 100 is modified to include an attachable sterilant enclosure 150 with the sterilant 118. Therefore, in this embodiment, the rack 114 and the sterilant housing 116 (See FIGS. 1A–5) shown in the previous embodiments are excluded. Accordingly, the sterilization container 100 is connected to the sterilant enclosure 150 by a connector 151. In this embodiment, a first end 154 of the connector 151 is connected to an opening 152 on the peripheral wall 104, while a second end 155 of the connector 151 is connected to the sterilant enclosure 150 through an optional valve 156 on the enclosure 150. A gas permeable membrane 158 further covers the opening 152 so that when the sterilant enclosure 150 is detached from the container 100, the sterility of the load in the container housing 106 is maintained. In the process of the present embodiment, the sterilant vapor from the sterilant source 118 passes through the valve 156 and gas permeable membrane 158 and enters the container 100 for sterilizing articles. For better diffusion, the inner tray 108 can have perforated walls. Similar to the previous embodiments, the biological and chemical indicators 122 and 124 can be attached to or detached from the container 100 without disturbing the sterility of the articles in the container 100.

Figure 6B:
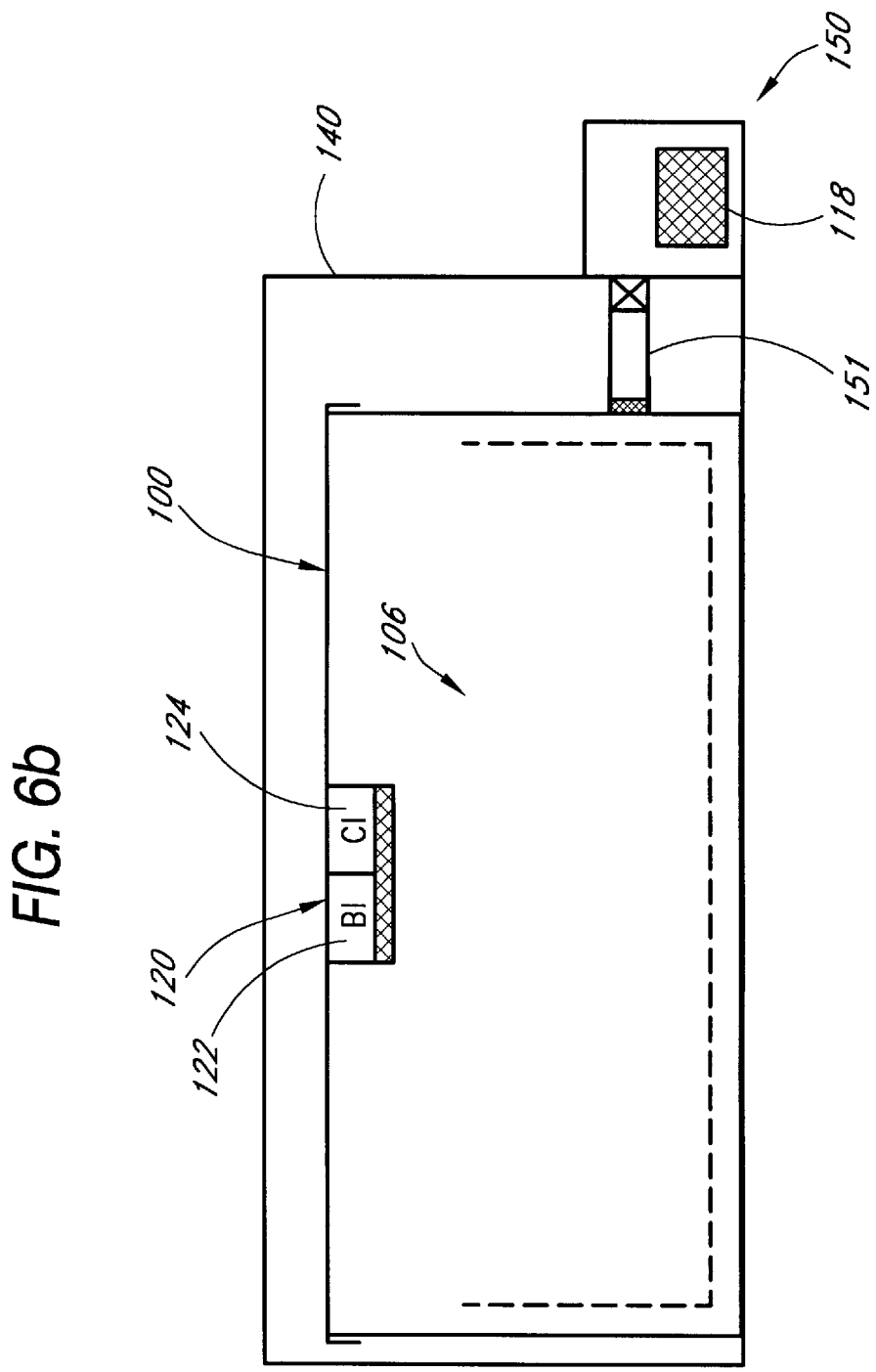
FIG. 6B is a schematic view of the sterilization system shown in FIG. 6A wherein the sterilization container with the separate sterilant enclosure is placed into a vacuum oven.

Within the scope of this invention, it will be appreciated that the present embodiment may also comprise all the features and options of the previous embodiments. For example, as in the second embodiment, the sterilant enclosure 150, as attached to the container 100, may be heated by a heat source to enhance the vaporization of the sterilant source 118 (See FIG. 2). Similar to the third, the fourth and the fifth embodiments, the container can be placed into a third container which may be an oven 132, vacuum chamber 136 or a vacuum oven 140 (See FIGS. 3–5). In all above embodiments, after the sterilization the sterilant enclosure 150 may be detached from the container 100 for storage purposes. Similarly, by suitable modifications in the oven 132, the vacuum chamber 136 and the vacuum oven 140, the sterilant enclosure may be integrated with the containers 132, 136 and 140. As illustrated in FIG. 6B, for example, when the container 100 is placed into the third container, such as a vacuum oven 140, the sterilant enclosure 150 is connected to the container 100 through conductor 151 as in the manner shown in FIG. 6B. The enclosure 150 can be heated to a different temperature than the vacuum oven 140.

Figure 7:
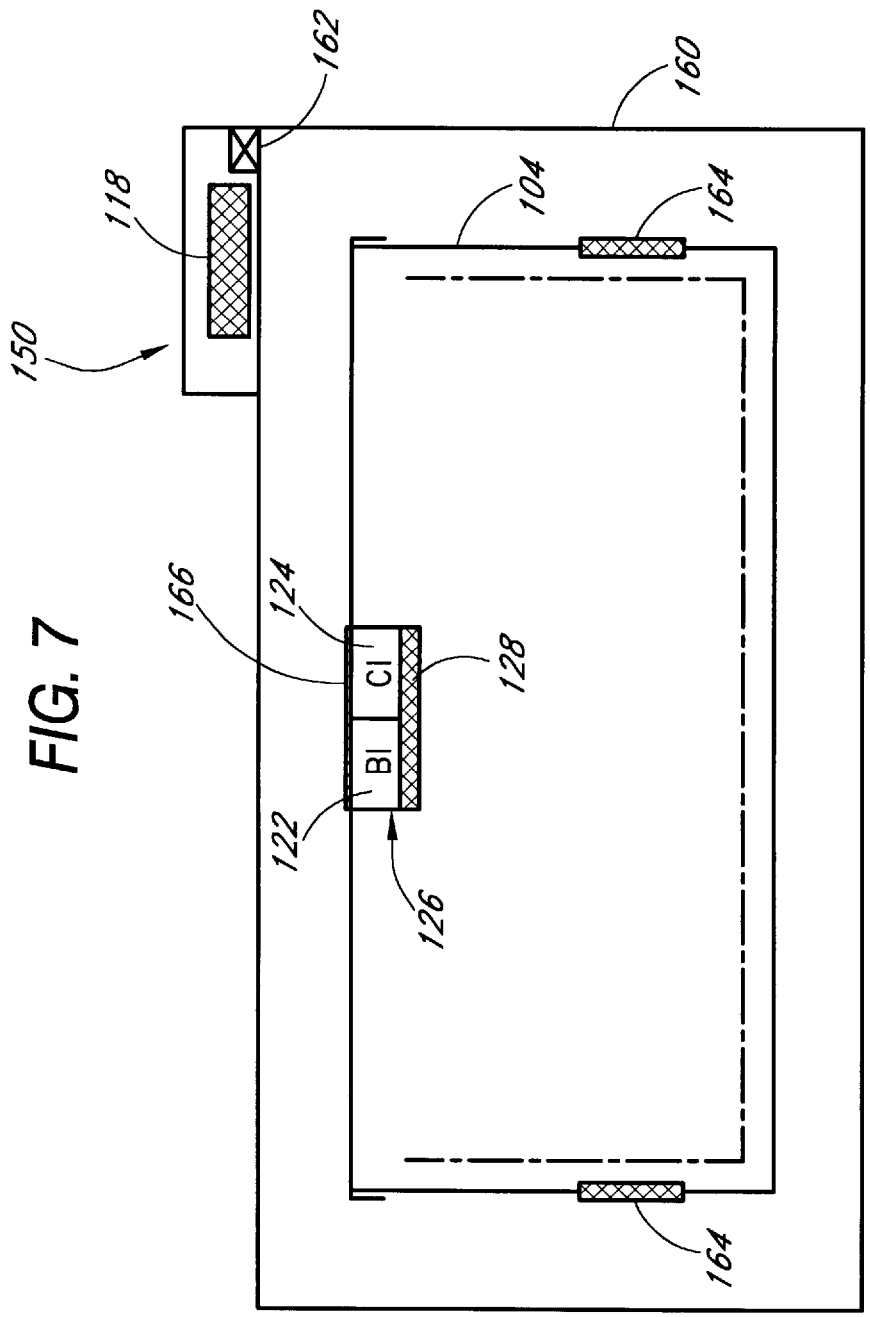
FIG. 7 is a schematic view of a seventh embodiment of the sterilization system wherein the sterilization container is placed into another container having an attached sterilant enclosure.

FIG. 7 shows a seventh embodiment of the sterilization system comprising the sterilization container 100 placed into a third container 160 and the enclosure 150 is attached to the container 160, such as by being an integrated part thereof. However, as opposed to previous embodiment, in this embodiment there is no direct connection between the sterilant enclosure 150 and the sterilant container 100. A number of gas permeable membrane covered inlets 164 are positioned on the peripheral wall 104 of the container 100. Further, top of the cartridge holder 126 may be sealed with a removable gas impermeable material 166 so as to expose indicators 122 and 124 only to the sterilant vapor diffusing through the gas permeable membrane 128. An exemplary gas impermeable material can be Mylar, metal foil, glass or adhesive tape. In the process of this embodiment, the sterilant gas first diffuses into the container 160 through inlet 162 and fills the container 160. The inlet 162 can be configured as a valve. As the process progresses, the sterilant gas diffuses from the enclosure 150 through the inlet 162 and into the container 160. From the container 160, the gas diffuses through the permeable membrane 164 into the container 100, through the permeable membrane 128 and into the cartridge 120, so as to contact the indicators 122 and 124. At the end of the process cycle, the gas impermeable material can be removed and the cartridge can be taken out for inspecting indicators 122 and 124.

As illustrated in FIG. 8, in an eighth embodiment, the sterilization system comprises the sterilization container 100 and the sterilant enclosure 150 as described in the sixth embodiment. In an effort to enhance the accuracy of the information provided from the indicators 122 and 124, in this embodiment, the cartridge holder 126 is positioned at a remotest location from the sterilant enclosure 150 containing sterilant source 118. Referring to FIG. 8, this location is on the peripheral wall 104 and at the opposite side of the container 100. A fan 160 can optionally be provided to circulate sterilant throughout the container 100. As previously explained, since the indicators 122 and 124 are the last place for sterilant vapor to reach, they provide an accurate method of monitoring the sterilization status of the articles inside the container 100.

As illustrated in FIG. 9A, in a first alternative embodiment, the sterilization system comprises an alternative container 200. In this embodiment, the alternative container 200 is preferably a flexible enclosed container, such as a pouch, which is comprised of a gas impermeable sheet material 202 defining a housing 204 to have articles to be sterilized (not shown). An exemplary gas impermeable sheet material may be preferably Mylar™, metal foil, polymer film materials such as polypropylene or polyethylene films. The flexible container 200 of this invention further comprise a first window 206, second window 208 and an opening 210. The first and second windows 206 and 208 are comprised of gas permeable materials, and preferably positioned at the opposite ends of the pouch 200. Articles to be sterilized are placed into the container 200 through the opening 210. This opening 210 may be a resealable opening for multiple use of the container 200 or may be a non-resealable opening for a single use.

A sterilant source cartridge 212 may be sealably placed onto the first gas permeable window 206 and secured using various fastening mechanisms such as double-sided tape, snap-on connectors or the like. As shown in FIG. 9B, the sterilant source cartridge 212 comprises a gas permeable bottom 216, a gas impermeable top 214 and peripheral side walls 213 defining a sterilant housing 215. For shipping and safe handling purposes, another gas impermeable layer 217 may be removably placed on the layer 216. However, before placing the cartridge onto the window 206, this impermeable layer 217 should be removed. In this embodiment, the gas permeable bottom 216 of the cartridge 212 is preferably sized and shaped to fit over the window 206. Referring to FIG. 9A, when the cartridge 212 is placed onto the gas permeable window 206, the bottom gas permeable layer 216 faces towards the window 206 on the flexible container 200. Therefore, when a sterilant source in the cartridge 212 releases a sterilant vapor, the vapor diffuses via the bottom layer 216 and the window 206 into the container 200 having articles to be sterilized.

As illustrated in FIG. 9C, a process monitoring cartridge 218 comprising the biological and chemical indicators 122 and 124 may be sealably placed onto the second gas permeable window 208, as in the manner described for the sterilant cartridge 212. As shown in FIG. 9C, the process monitoring cartridge 218 is comprised of a gas permeable bottom 220, a gas permeable removable top 221 and a body 222 comprising the biological and/or chemical indicators 122 and 124. In operation, the sterilant gas released from the sterilant cartridge 212 diffuses into the container housing 204 (in the direction of the arrows) and reaches at the monitoring cartridge 218 through the gas permeable window 208. Similar to previous embodiments, the flexible container 200 of the present invention can be also used in the oven 132, the vacuum chamber 136 or a vacuum oven 140.

Figure 9D:
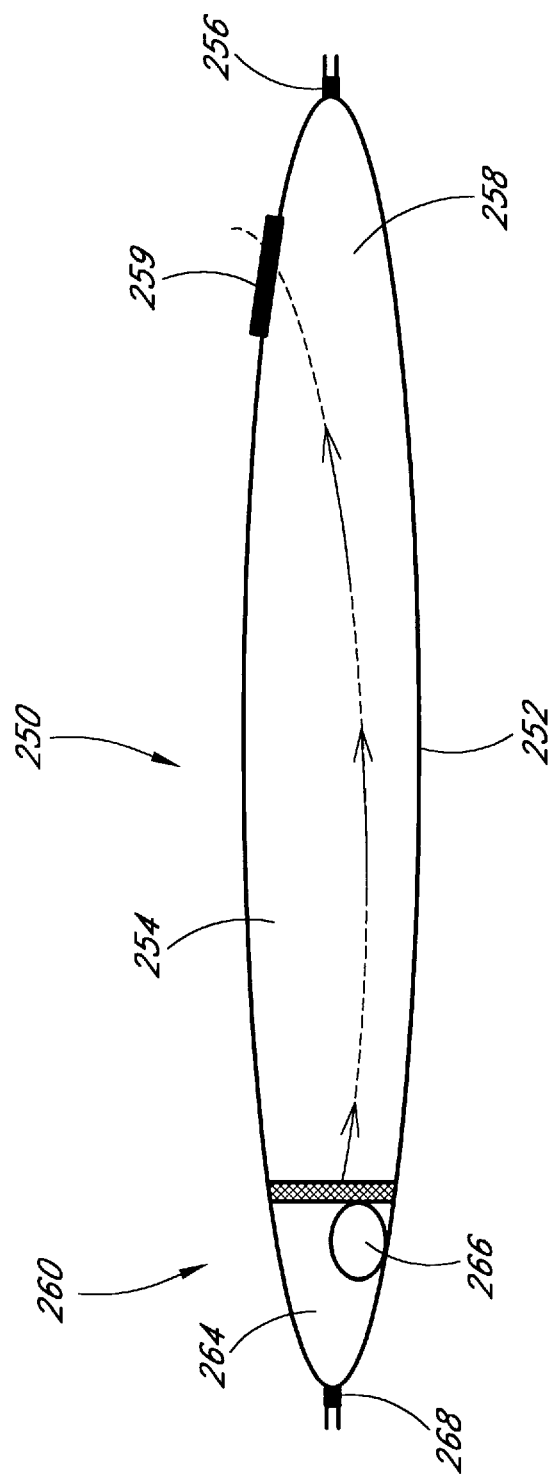
FIG. 9D is a schematic view of another alternative embodiment of the sterilization system with one window and sterilant inside a pouch behind a gas permeable membrane.

As illustrated in FIG. 9D, in a second alternative embodiment, the sterilization system comprises a flexible enclosed container 250. Similar to the pouch 200 of the previous embodiment, the flexible container 250 also comprises a gas impermeable sheet material 252 (such as those materials given above) defining a container housing 254 and an opening 256 to place articles (not shown) into the container 250. However, in this embodiment, the container 250 comprises only one gas permeable window 258 on which a process monitoring cartridge 259 is placed, and a sterilant enclosure 260 attached to a gas permeable wall portion 262 of the flexible container 250. In this embodiment, the sterilant enclosure 260 is preferably a flexible sterilant enclosure comprising a sterilant housing 264 which is separated from the container housing 254 by the gas permeable wall portion 262. A sterilant source 266 may be placed into the housing 264 through an optional opening 268. This optional opening 268 may be a resealable opening for multiple use of the container 250 or may be a non-resealable opening for a single use. Similar to the previous embodiment, in operation, the sterilant gas released from the sterilant source 266 diffuses through the gas permeable wall portion 262 into the container housing 254, and reaches at the monitoring cartridge 259 (following arrows in FIG. 9D) through the gas permeable window 258.

It will be appreciated that, in all above embodiments, upon completion of the sterilization cycle the process monitor cartridge can be advantageously removed from system to determine chemical and biological efficacy of the sterilization process. As opposed to prior art systems, however, the removal of the biological and chemical indicators does not disturb the sterilized state of the articles inside the sterilization container. Since the gas permeable layer only allows the passage of the sterilant vapor, removal of the cartridge from the sterilizing container will not break the sealed status of the container.

Hence, although the foregoing description of the preferred embodiment of the present invention has shown, described and pointed out the fundamental novel features of the invention, it will be understood that various omissions, substitutions, and changes in the form of the detail of the apparatus and method as illustrated as well as the uses thereof, may be made by those skilled in the art, without departing from the spirit of the present invention. Consequently, the scope of the present invention should not be limited to the foregoing discussions, but should be defined by the appended claims.

What is claimed is:

1. A system for monitoring a sterilization process comprising:
   a container having an interior space to receive articles to be sterilized wherein said container comprises at least one gas permeable material on an outer wall of said container so as to allow a sterilant gas to diffuse from said interior space through said gas permeable material;
   a sterilant source adapted to provide said sterilant gas in said interior space; and
   at least one indicator wherein said indicator is positioned adjacent said at least one gas permeable material so that said indicator is in fluid communication with said interior space through said gas permeable material to receive said sterilant gas that diffuses through said gas permeable material, and wherein said gas permeable material prevents the penetration of microorganisms therethrough so that said at least one indicator can be removed from said container without disturbing sterility of the articles within the container.

2. The system of claim 1, wherein said gas permeable material is spun-bond polyethylene or non-woven polypropylene.

3. The system of claim 1, wherein said outer wall of said container defines a cartridge opening such that a first surface of said cartridge opening is said gas permeable material, and wherein said at least one indicator is placed into a cartridge.

4. The system of claim 3, wherein said cartridge has a gas permeable material and is positioned in said cartridge opening so that said gas permeable material of said cartridge is in fluid communication with the gas permeable material of said cartridge housing.

5. The system of claim 1, wherein said indicator is placed within an enclosure having an openable or removable top.

6. The system of claim 5, wherein said top is translucent or clear.

7. The system of claim 3, wherein said cartridge comprises a clear or translucent top.

8. The system of claim 1, wherein said indicator is a biological indicator.

9. The system of claim 1, wherein said indicator is a chemical indicator.

10. The system of claim 1, wherein said system additionally comprises a fan adapted to circulate sterilant gas inside said container.

11. The system of claim 1, wherein said container is a flexible pouch made of a gas impermeable material.

12. The system of claim 11, wherein said pouch further comprising a first window and a second window, each of said windows comprised of gas permeable material.

13. The system of claim 1, wherein said sterilant source is a liquid sterilant source.

14. The system of claim 13, wherein said liquid sterilant source is liquid hydrogen peroxide or peracetic acid.

15. The system of claim 1, wherein said sterilant source is a solid sterilant source.

16. The system of claim 15, wherein said solid sterilant source is urea hydrogen peroxide complex or a sodium pyrophosphate hydrogen peroxide complex.

17. The system of claim 1, wherein said sterilant source is placed inside said sterilization container.

18. The system of claim 1, wherein said sterilant source is placed into an enclosure in fluid communication with said interior space.

19. The system of claim 18, wherein said container is detachable from said enclosure.

20. The system of claim 19, additionally comprising a connector between said enclosure and said interior space.

21. The system of claim 1, wherein said sterilant gas is produced by applying heat to said sterilant source.

22. The system of claim 1, wherein said sterilant gas is produced by applying vacuum to said sterilant source in an vacuum chamber.

23. The system of claim 1, additionally comprising a plasma generator adapted to provide plasma in or to said container.

24. The system of claim 1, wherein the indicator and the container each contain a unique identifier pairing the indicator with the container.

25. A method of monitoring a sterilization process comprising:
   providing a container having an interior space to receive articles to be sterilized, wherein said container comprises at least one gas permeable material on an outer wall of said container in fluid communication with said interior space so as to allow a sterilant gas to diffuse through said gas permeable material;
   providing a sterilant source adapted to provide said sterilant gas inside of said container; and
   positioning at least one indicator exterior of said interior space in fluid communication therewith through said gas permeable material of said container so that said indicator receives said sterilant gas that diffuses through said gas permeable material from said interior space, and wherein said gas permeable material prevents the penetration of microorganisms therethrough so that said at least one indicator can be removed from said container without disturbing sterility of the articles within the container.

26. The method of claim 25, wherein said at least one indicator is placed into a cartridge, and wherein said cartridge is positioned in said cartridge opening so that said gas permeable region is in fluid communication with said cartridge having said at least one indicator.

27. The method of claim 25, wherein said indicator is a biological indicator, and additionally comprising the step of assaying said biological indicator for the presence or absence of microorganisms to determine if sterilization has occurred.

28. The method of claim 25, wherein said indicator is a chemical indicator, and additionally comprising the step of identifying a chemical change in said chemical indicator to indicate that a sterilization process has been completed.

29. The method of claim 25, wherein said sterilant source is a solid sterilant source, and additionally comprising the step of heating said solid sterilant source or exposing said solid sterilant source to vacuum so as to release sterilant gas therefrom.

30. The method of claim 25, wherein said sterilant source is placed into an enclosure and said enclosure is placed into fluid communication with said interior space.

31. The method of claim 30, additionally comprising attaching said container to said enclosure through a connector and flowing sterilant gas released inside said enclosure through said connector to said sterilization container.

32. The method of claim 25, additionally comprising generating a plasma and contacting said articles with said plasma.

* * * * *

UNITED STATES PATENT AND TRADEMARK OFFICE
CERTIFICATE OF CORRECTION

PATENT NO. : 5,834,313
DATED : November 10, 1998
INVENTOR(S) : Lin Szu-Min and Paul Taylor Jacobs It is certified that error appears in the above-identified patent and that said Letters Patent is hereby corrected as shown below:

On the title page, Item [75], please add the second inventor --Paul Taylor Jacobs, TRabuco Canyon, California.--.

Item [19], "Lin" should read --Lin, et al..--

Signed and Sealed this

Twenty-second Day of June, 1999

Attest:

Q. TODD DICKINSON

*Attesting Officer*     Acting Commissioner of Patents and Trademarks